United States Patent [19]

Lorenz et al.

[11] 4,365,640
[45] Dec. 28, 1982

[54] EQUIPMENT FOR SMOKING SMOKABLE OBJECTS

[75] Inventors: Hans-Walther Lorenz, Hamburg; Gerd Schumacher, Pinneberg, both of Fed. Rep. of Germany

[73] Assignee: B.A.T. Cigaretten-Fabriken GmbH, Hamburg, Fed. Rep. of Germany

[21] Appl. No.: 194,353

[22] Filed: Oct. 6, 1980

[30] Foreign Application Priority Data

Oct. 4, 1979 [DE] Fed. Rep. of Germany ....... 2940280

[51] Int. Cl.³ .................. A24F 13/00; A24F 13/22
[52] U.S. Cl. .................................. 131/330; 131/328; 73/432 SD
[58] Field of Search .............................. 131/328, 330; 73/432 SD

[56] References Cited

PUBLICATIONS

*Smoking Behavior* edited by Raymond Thornton, Churchill Livingstone, Edinburgh, London and New York, 1978, pp. 277–288 cited.
Die Tabak, Zeitung Nr. 20/Seite 6.

*Primary Examiner*—V. Millin
*Attorney, Agent, or Firm*—Armstrong, Nikaido, Marmelstein & Kubovcik

[57] ABSTRACT

An apparatus for simulating a human smoking a smokable object which comprises an inhaling device for drawing smoke from the object and a motor which is coupled to the inhaling device for driving the inhaling device. The apparatus further comprises a control circuit for controlling the operation of the motor. The control circuit includes a circuit for receiving an analog signal corresponding to a human draw profile of the smoking of the object, a converter coupled to the receiving circuit for converting the analog signal to a pulse signal and a switching device for applying the pulse signal to the motor for controlling the operation of the motor.

10 Claims, 5 Drawing Figures

EQUIPMENT FOR SMOKING SMOKABLE OBJECTS

BACKGROUND OF THE INVENTION

1. Field of the Invention

The invention relates to equipment for smoking cigarettes, using a smoking machine which is activated as a function of a test-person's recorded inhaling, or draw-profiles.

Such apparatus is used to collect the substances contained in the cigarette smoke to subsequently feed them to an analysis stage. In this manner it is possible to compare various kinds of cigarettes and also various batches of one kind of cigarette as regards the smoke composition. It is essential in this respect that the smoking process correspond as much as possible to the habits of the smoker and that, therefore, various pauses, durations and intensities in the inhaling be considered.

2. Description of the Prior Art

Equipment of the cited species is known from the book SMOKING BEHAVIOR by Raymond E. Thornton, Churchill Livingstone publishers, 1978, pp 277 through 288. The pressure and volume profiles of the smoking gas generated when a test person smokes a cigarette are measured and converted into electric potential values, subjected to an analog-digital conversion and stored on magnetic tape, also including the pauses in inhaling; this stored draw profile can be read out from the magnetic tape to activate a smoking machine.

By means of a partial vacuum, this smoking machine generates the required air flow for the smoking of a cigarette, this flow being controlled by an analog valve.

The potential values obtained and recorded in the above-mentioned manner are used to control the valves inserted into the smoking channels between a partial-vacuum chamber and a cigarette, the valves opening or closing more or less depending on the particular values of the recorded draw profile and hence draw an amount of gas through the cigarette which corresponds to the test-person's draw profile.

The known apparatus suffers from the drawback that the application of the recorded draw profile and especially the control of such a smoking machine is very costly; and in spite of this high cost, the profile generated in the smoking machine will not always correspond in all aspects to the test-person's draw profile. Difficulties occur for instance, when a double-draw should be reproduced as occurs when starting a cigarette. In such a double-draw, there is a very rapid rise and fall of the draw profile that can hardly be simulated by means of valves.

SUMMARY OF THE INVENTION

It is, therefore, the object of the present invention to provide an apparatus of the cited species which shall be free of the above-mentioned drawbacks.

In particular, it is the object of the present invention to provide an apparatus whereby all recorded draw profiles, especially also double-draws, can be reproduced very accurately.

The present invention solves this problem with an apparatus for generating and applying control signals corresponding to the draw profiles to a stepping motor driving a piston smoking machine.

The advantages obtained by the present invention, in particular, are based on the fact that the stepping motor for driving the flask smoking machine can be activated very exactly, that is in a well defined manner, whereby the motion generated by the stepping motor will be a very precise reproduction of the recorded draw profile. This motion in turn is transmitted to the piston of a flask smoking machine which also can be displaced very accurately, so that overall there will be a very reliable and accurate reproduction of the recorded draw profile.

Complex profiles, for instance double-draws and simple very flat, short draws can be reproduced very accurately with respect to intensity, duration and steepness, whereby the apparatus of the present invention makes possible the simulation of all human draw profiles occurring in practice.

Appropriately controlled magnetic valves are located in the smoking channels of the flask smoking machine; they are not used to adjust the flow rate but rather only to open or close the smoking channels. Furthermore, a bypass line should be provided in the cigarette holder, communicating with the atmosphere, which can be suitably blocked by a further magnetic valve. In this manner, communication with the atmosphere can be established, thereby simulating the condition in which the smoker takes the cigarette out of his mouth and the flow from the glow can move into the atmosphere on account of the temperature drop in the cigarette (the so-called open smoking).

BRIEF DESCRIPTION OF THE DRAWINGS

The invention is explained below in relation to an embodiment and to the enclosed, schematic drawings.

Figure 1:
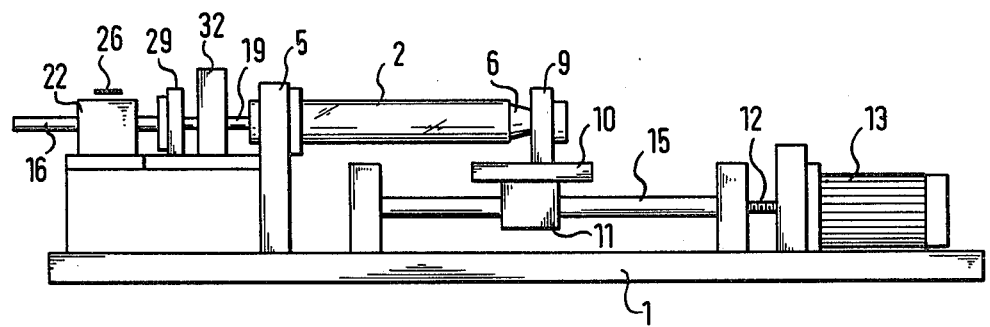
FIG. 1 is a side view of the flask smoking machine of the present invention.
Figure 2:
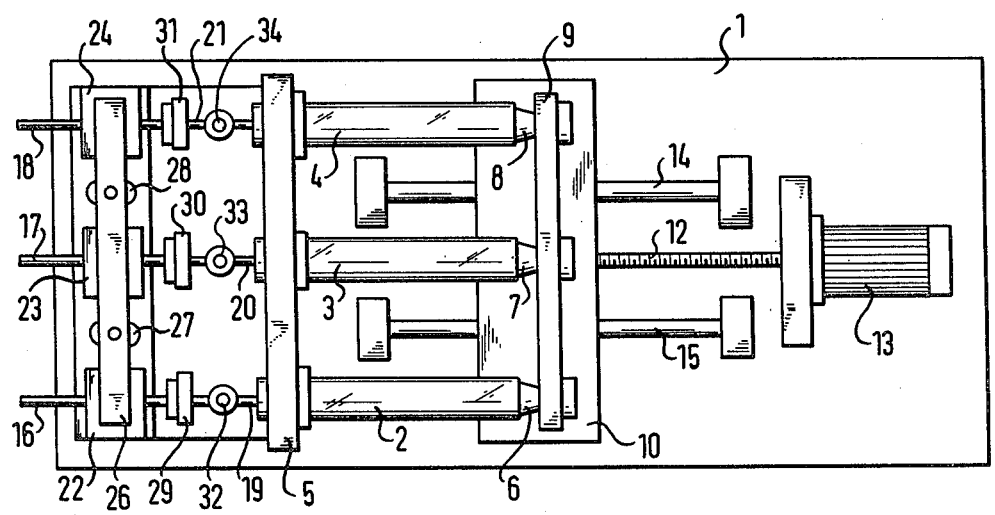
FIG. 2 is a top view of the flask smoking machine of the present invention.

As can be seen from FIGS. 1 and 2, three glass flasks 2, 3 and 4 are held in a common support block 5 on a base plate 1. The flask pistons 6, 7 and 8 are mutually connected by a crossbar 9 which in turn is fastened to a plate 10. At the lower side of plate 10 is located the support 11 which is driven by a threaded spindle 12 of a stepping motor 13 also mounted to base plate 1. The support 11 and thus the flask pistons 6, 7 and 8 are guided by two steel shafts 14 and 15 which are mounted parallel to the spindle 12.

Smoking channels 19, 20 and 21 starting at th cigarettes 16, 17 and 18, which are being smoked, issue into the front ends, i.e., those ends of the glass flasks 2, 3 and 4 which are away from the stepping motor 13. Cigarettes 16, 17 and 18 are fastened in cigarette-holders 22, 23 and 24 which each comprise a bypass, (not shown) which communicates with the atmosphere. To cover and hence to seal this bypass, two solenoids 27 and 28 act with the plate 26. Filters 29, 30 and 31 which are Cambridge filters and magnetic valves 32, 33 and 34 are inserted into the smoking channels 19, 20 and 21.

The equipment basically operates as follows: First, the flow volume of the smoke inhaled by a test person is measured in a manner shown per se and not shown in further detail by the pressure difference generated by a flow resistance and converted into a proportional potential signal and stored on an analog casette recorder. When reproducing these stored potential signals from the analog casette recorder, the correspondingly amplified potential signal is fed to a voltage-frequency converter which generates control pulses for the stepping motor 13. The angular speed of the stepping motor is proportional to the potential signal, that is, the number of rotational steps of the drive shaft of stepping motor 13 is proportional to the corresponding, instantaneous value of the flow volume, whereby the drive shaft of the stepping motor rotates in accordance with the draw profile of the test person.

The rotational motion of the drive shaft of the stepping motor is converted by spindle 12 into linear motion which correspondingly displaces the support 11 connected to the flask pistons. Thus, the motion of the flask pistons also takes place which is proportional to the potential signal and hence to the corresponding instantaneous flow volume, whereby the glass flasks generate a draw profile precisely corresponding to the flow profile at the test-person's cigarette.

Therefore, such an apparatus is termed a "puff duplicator".

The details of the control and operation will be provided below in relation to FIGS. 3 through 5.

The shape of the potential signal $U_e$ corresponds to the draw profile of the test person, that is, to the flow rate of the test-person's cigarette smoke. The absolute value $|U|$ of this potential signal $U_e$ is formed in a circuit 40. This magnitude $|U|$ of the potential signal $U_e$ on one hand is applied through a null comparator 41 to the relay logic circuit 43, to be discussed below, the control the profile generation, and on the other hand to an integrator (not shown), which selectively displays the integrals of the draw-profiles to be controlled (master signals) or of the reproduced draw profiles (slave signals). The response threshold of the null comparator 41 can be set by means of a potentiometer 42 to eliminate any noise levels.

The circuit 40, furthermore, is connected by another potentiometer 44, for any required signal attenuation, to another integrator 45.

The output signal from the integrator 45 is applied through a voltage-frequency converter 46 to a control-set 47, which receives signals from the relay logic circuit 43, and controls the stepping motor 13 which moves forward, backward or stands still depending on the magnitude of the potential signal $U_e$ and the position of the flask pistons 6 through 8.

Two limit switches GSL and GSR actuated by the flask pistons 6, 7 or 8 are essential for the above cited motion; these limit switches open when the flask pistons 6, 7 and 8 are in their left or right end positions, and they stop the stepping motor 13 by means of the relay logic circuit 43 and close the magnetic valves 32, 33 and 34 and bypasses 22, 23 and 24 by means of solenoids 27 and 28.

Figure 3:
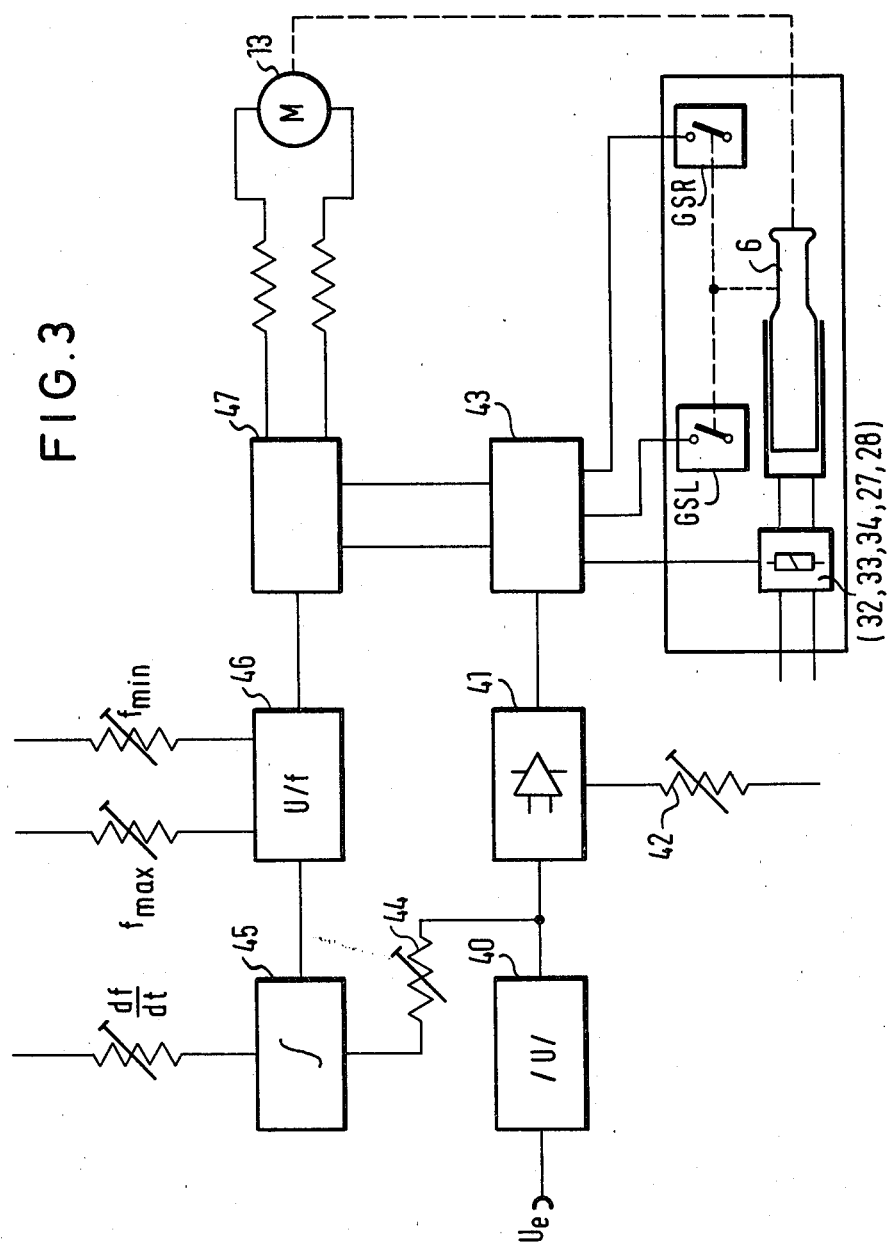
FIG. 3 is a block circuit diagram of the flask smoking machine control circuit of the present invention.
Figure 4:
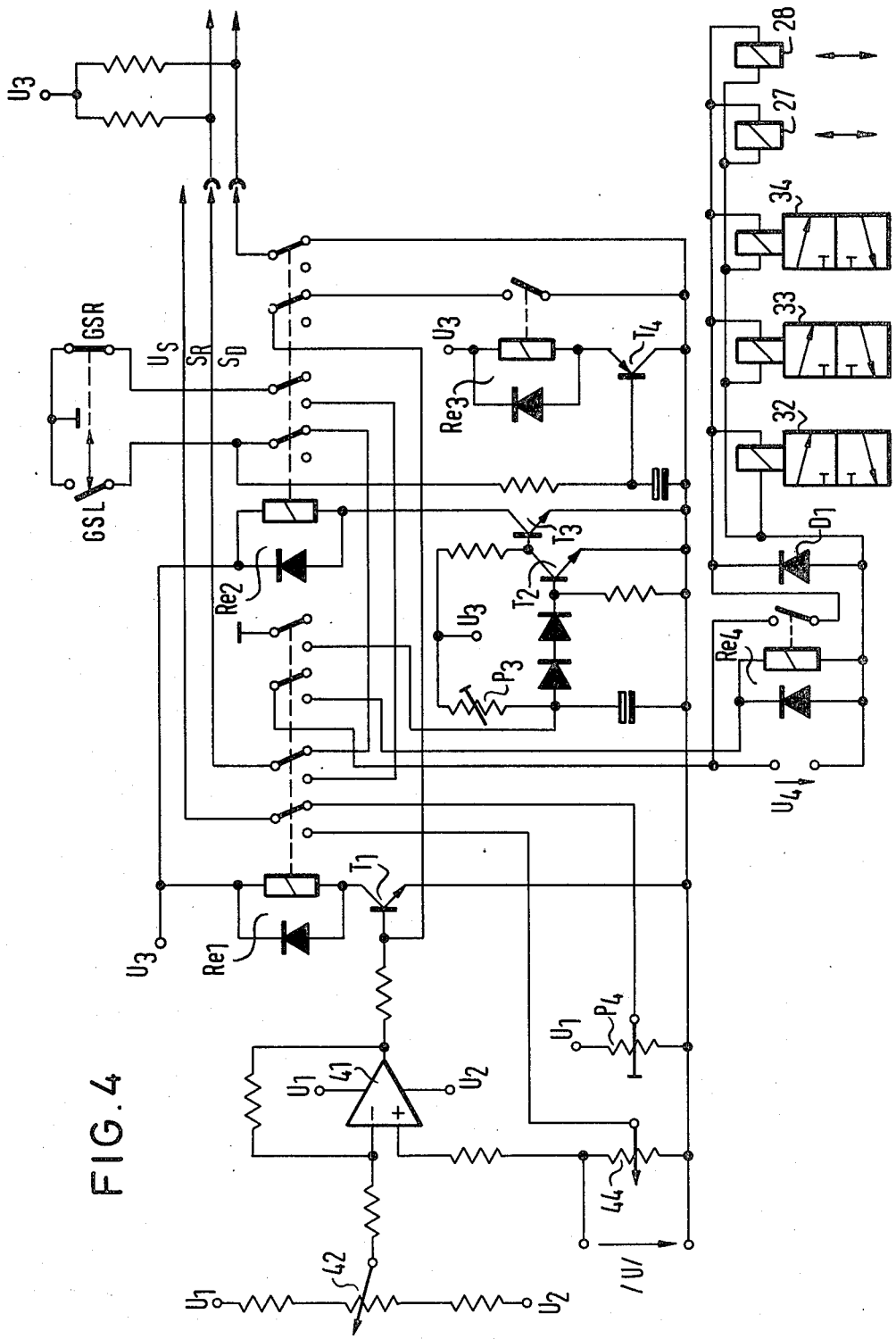
FIG. 4 is a detailed view of the relay logic for the control circuit.

The essential particulars of the stepping-motor control circuit, consisting of circuit 40, null comparator 41, relay logic circuit 43, limit switches GSL and GSR and solenoid valves 32, 33 and 34 also indicated in FIG. 3, are shown in the circuit diagram of FIG. 4.

In the illustrative embodiment shown, the preferred rotation for the stepping motor 13 is clockwise, that is, "exhaling" by the flask smoking machine, while the waiting and starting position is the left-side end position of the flask pistons 6, 7 and 8, i.e., the left-side limit switch GSL is open. As indicated in the circuit diagram of FIG. 4, three signals are generated as a function of the positions of the limit switches GSL and GSR and the presence of the potential signal $|U|$, namely, the control signal $U_s$, the RUN signal $S_r$ and direction-of-rotation signal $S_d$, which are fed to the control circuit 47 (omitted from the circuit diagram).

The circuit shown in FIG. 4 operates as follows: in the presence of an analog potential signal $U_e$ at the circuit 40, the absolute value $|U|$ of signal $U_e$ is formed; this absolute value is compared in the null comparator 41 with a response threshold that can be adjusted by the potentiometer 42. If the response threshold is exceeded, the null comparator 41 generates a rectangular pulse acting on a driver transistor $T_1$ so that the relays $Re_1$ and $Re_4$ are energized and hence the analog potential signal $|U|$ is present as the control signal $U_s$, while the RUN signal $S_r$ remains interrupted. Also, the magnetic valves 32, 33 and 34 and the solenoids 27 and 28 switch on. Almost synchronously therewith, a relay $Re_2$ energizes, whereby the stepping motor is reversed to counterclockwise rotation and the RUN signal $S_r$ is emitted. This switching position remains until the termination of the analog signal $U_e$ or until the response threshold of the null comparator no longer is exceeded.

If now the flask pistons 6, 7 and 8 move out of their left end positions, the left-side limit switch GSL will close and a relay $Re_3$ is energized with a delay, thereby turning off the driver transistor $T_1$ for the relay $Re_1$; the turning off of $T_1$ is implemented at once if the relay $Re_2$ is de-energized.

If now the analog potential signal $U_e$ is terminated, the relay $Re_1$ is de-energized and interrupts first the RUN signal $S_r$. Simultaneously, the control signal $U_2$ is switched to a return motion potential which can be adjusted through the potentiometer $P_4$ and the de-energization of relay $Re_2$ is initiated. The relay $Re_2$ is de-energized after a delay time that can be set by means of the potentiometer $P_3$ and the stepping motor 13 is switched on by reversing the direction-of-rotation signal $S_d$ to clockwise rotation. Simultaneously, the RUN signal $S_r$ is generated whereby the stepping motor and hence the flask pistons 6, 7 and 8 return to their initial positions.

Simultaneously with the de-energization of the relay $Re_4$, the solenoids 27 and 28 and the magnetic valves 32, 33 and 34 are switched off. The relays $Re_1$ and $Re_2$ are now protected by the relay $Re_3$ against renewed energization.

Thus, the switching process and the motions so caused have the effect that the flask smoking machine takes the cigarettes "out of the mouth" and the smoke located in the glass flasks 2, 3 and 4 is "exhaled" into the atmosphere by the switched-over magnetic valves 32, 33 and 34.

The flask pistons 6, 7 and 8 now move at a constant speed back into their left-side end position and thereby open the left-side limit switch GSL. First, the RUN signal $S_r$ is interrupted thereby. If next the relay $Re_3$ is de-energized with a delay, the initial position is re-established and the flask smoking machine is ready for inhaling again.

If a further analog signal $U_e$ is present within the de-energizing delay of relay $Re_2$, representing a double-draw such as occurs for instance when lighting a cigarette, then only the relays $Re_1$ and $Re_4$ are energized again, whereby the stepping motor 13 continues to run counterclockwise. For this operational state, the flask smoking machine therefore, takes the "cigarette out of the mouth" without the aspirated smoke being "exhaled".

If the flask pistons 6, 7 and 8 on account of a single or double draw or by faulty operation move to the right-side end position, then the right-side limit switch GSR opens and interrupts the RUN signal $S_r$, i.e., the flask smoking machine "holds its breath" until the analog potential signal $U_e$ reaches zero.

These particular motion sequences will be discussed comprehensively again below in reference to FIG. 5, which shows the analog signal and the control signals that result from it as a function time.

Figure 5:
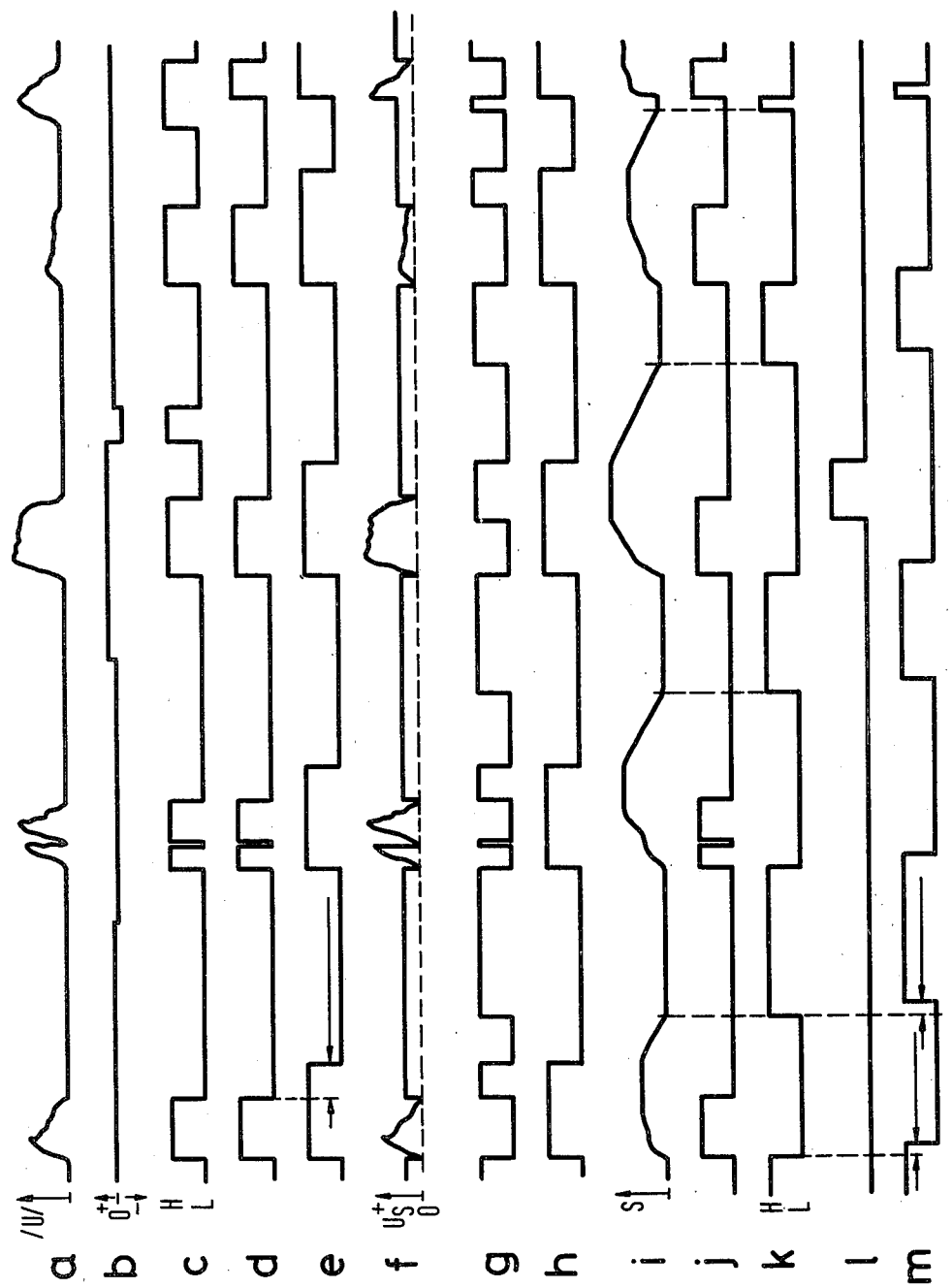
FIGS. 5a through 5m are waveshapes of the various signals of the control circuit.

Curve (a) of FIG. 5 shows, from left to right, together with the typical pauses between drawing in, the following different draw profiles:

(A) a typical draw profile within the predetermined range of reproduction, (B) a typical double-draw profile as occurs especially when starting to smoke; the total volume corresponding to this profile also is within the range of reproduction, (C) an excessive draw profile outside the range of reproduction, and (D) a flat draw profile, within a processing cycle in which there is some interference, in this case for instance another draw profile. In this instance, the smoking machine terminates the cycle just ending and starts again with the instantaneous value of the analog signal. This situation does not occur in practice, but is meant merely to emphasize that even spurious signals cannot degrade the logic operation; thus, when calibrating the apparatus, signals in brief succession may be simulated.

The absolute magnitude $|U|$ of the analog signal $U_e$ is recorded in curve (a) of FIG. 5, the absolute value of the potential signal $U_e$ being formed in the circuit 40 so that the signals obtained can be processed even for an erroneously reversed pressure-difference pickup.

The control signals derived from the particular signals are plotted below curve (a) as in curves (b) through (m).

Curve (b) shows the level of the response threshold which is set by the potentiometer 41 for a variety of values.

Curve (c) shows a rectangular pulse from which, in conjunction with the switch positions of the two limit switches GSL and GSR, all the other control signals are formed. This rectangular pulse is the output signal from the null comparator 41.

This rectangular pulse obeys the equations:

$|U|+U_s>0 \rightarrow H$ (open switch)

$|U|+U_s \leqq 0 \rightarrow L$ (closed switch).

Curve (d) shows the switching positions of relay $Re_1$, which is energized only when relay $Re_3$ (curve (m)) is de-energized and the rectangular pulse of curve (c) is present.

Curve (e) shows the switching positions of the relay $Re_2$. The relay $Re_2$ is energized by the relay $Re_1$ and is de-energized with a delay of about 1 second after the relay $Re_1$ is de-energized.

Curve (f) shows the actual control signal $U_s$ for the stepping motor 13. The angular speed of the stepping motor is proportional to this signal.

Curve (g) shows the RUN signal $S_r$. The stepping motor 13 only runs when this RUN signal is at the "L" level, i.e., when its value is low. This will only be the case when the relay $Re_1$ (curve (d)) and relay $Re_2$ (curve (e)) are energized and the right-side limit switch GSR (curve (l)) is closed, or when both relays $Re_1$ and $Re_2$ are de-energized and the left-side limit switch GSL is closed.

Curve (h) shows the direction of rotation of the stepping motor 13, i.e., either counterclockwise or clockwise. It can be seen that this signal changes synchronously with the position of the relay $Re_2$ (curve (g)). This means that the direction of rotation of the stepping motor 13 will only be reversed after it is safely stopped.

Curve (i) plots the path-time diagram of the tips of the flask pistons 6, 7 and 8. This curve corresponds to the integral of the control signal $U_s$ (curve (f)), taking into account the RUN and direction-of-rotation signals (curves (h) and (g)).

Curve (j) shows the switching position of the relay $Re_4$ which is energized by the relay $Re_1$ (curve (d)). The three magnetic valves 32, 33 and 34 and the two solenoids 27 and 28 are energized by the relay $Re_4$.

The curve (k) represents the switching position of the left limit switch GSL and curve (l) that of the right limit switch GSR. As already mentioned above, these switching positions depend only on the location of the tips of the flask pistons 6, 7 and 8 the particular limit switches being open when the related piston is in the end position.

Lastly, curve (m) indicates the switching position of the relay $Re_3$, which is energized and de-energized with a delay with respect to the left-side limit switch GSL (curve (k)).

These curves show that the accurate reproduction of the recorded draw profile depends not only on the time and rate of the running of the stepping motor 13, but that in addition the valves provided in the smoking channels switch off accurately at the end of each analog signal, whereby a precisely defined smoking phase is obtained. Thereby, an optimal duplication of human smoking is made possible, whereby the residues ascertained are also representative of the actual smoking.

The present invention may be embodied in other specific forms without departing from the spirit or essential characteristics thereof. The presently disclosed embodiments are, therefore, to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed is:

1. An apparatus for simulating a human smoking a smokable object comprising:
   (a) inhaling means for drawing smoke from said object;
   (b) motor means coupled to said inhaling means for driving said inhaling means; and
   (c) control circuit means for controlling the operation of said motor means, said control means including means for receiving an analog signal corresponding to a human draw profile of the smoking of the object, converter means coupled to said receiving means for converting said analog signal to a pulse signal and switching means for applying said pulse signal to said motor means for controlling the operation of said motor means.

2. An apparatus as set forth in claim 1, wherein said motor means is a stepping motor.

3. An apparatus as set forth in claim 1, wherein said inhaling means comprises piston means for drawing smoke into a piston chamber means thereof.

4. An apparatus as set forth in claim 3, including bypass means coupled to said piston means for venting smoke therein into the atmosphere.

5. An apparatus as set forth in claim 4, wherein said control circuit means includes solenoids for controlling the operation of said bypass means.

6. An apparatus as set forth in any of claims 1–5, wherein said control circuit means comprises:

(a) absolute circuit means for taking the absolute value of the analog signal corresponding to the human draw profile;

(b) comparator means coupled to the output of said absolute circuit means for comparing the output of said absolute circuit means to a predetermined value and for producing an output when the output of said absolute circuit is greater than said predetermined value;

(c) relay logic means coupled to the output of said comparator means for energizing and de-energizing a plurality of solenoid means in response thereto;

(d) integrator means coupled to the output of said absolute circuit means;

(e) voltage-frequency converter means coupled to the output of said integrator means for converting the output thereof; and (f) motor control set means coupled to said voltage-frequency converter means and said relay logic means, wherein said motor set control means controls the operation of said motor means.

7. An apparatus as set forth in claim 3, wherein said piston means includes a plurality of pistons and said piston chamber means includes a plurality of flasks and wherein said plurality of pistons are moved simultaneously in said flasks by said motor means.

8. An apparatus as set forth in claim 7, wherein said inhaling means includes support plate means for supporting all of said flasks.

9. An apparatus as set forth in claim 6, including limit switch means coupled to said relay logic means for providing an indication of the end positions of movement of said piston means wherein said stepping motor is stopped upon the actuation of said limit switch means.

10. An apparatus as set forth in claim 9, wherein said relay logic means includes first and second relays for operating simultaneously in response to a received signal wherein upon operation of said relay logic means said control circuit provides a control signal, a run signal and a direction of rotation signal to said motor means.

* * * * *